United States Patent [19]

Fields et al.

[11] 4,436,940

[45] Mar. 13, 1984

[54] PHOTOCHEMICAL METHOD FOR PREPARING LOW MOLECULAR WEIGHT OLEFIN POLYMERS AND COPOLYMERS OF 3-BUTENE-1-OL

[75] Inventors: Ellis K. Fields, River Forest; William C. Clarke, Evanston, both of Ill.

[73] Assignee: Standard Oil Company (Indiana), Chicago, Ill.

[21] Appl. No.: 256,060

[22] Filed: Apr. 21, 1981

[51] Int. Cl.³ .............................................. B01J 19/12
[52] U.S. Cl. ................................. 568/857; 204/158 R; 204/162 R; 568/816
[58] Field of Search ...................... 204/158 R, 162 R; 568/857, 816, 823

[56] References Cited

U.S. PATENT DOCUMENTS 3,324,187 6/1967 Litt et al. ............................. 260/633

OTHER PUBLICATIONS

Organic Photochemistry, Edited by O. C. Chapman, vol. 1, (1967), p. 292, Macel Dekker, Inc., N.Y.

*Primary Examiner*—Howard S. Williams
*Attorney, Agent, or Firm*—William C. Clarke; William T. McClain; William H. Magidson

[57] ABSTRACT

Low molecular weight olefin polymers and copolymers of 3-butene-1-ol of molecular weights within range of from about 200 to about 4000.

18 Claims, No Drawings

PHOTOCHEMICAL METHOD FOR PREPARING LOW MOLECULAR WEIGHT OLEFIN POLYMERS AND COPOLYMERS OF 3-BUTENE-1-OL

FIELD OF THE INVENTION

The field of this invention relates to low molecular weight polymers useful in enhanced oil field recovery which act as cosurfactants and function as coupling agents.

This invention relates to low molecular weight olefin polymers and copolymers of 3-butene-1-ol with molecular weights within range of from about 200 to about 4000. These low molecular weight polymers are prepared by photochemical reaction of aliphatic ketones with aliphatic and alicyclic olefins and are useful as additives for enhanced oil recovery. These polymers are also useful as surfactants and biocides, and can be used as hydraulic fluids, chemical intermediates and perfume components.

Cosurfactants function as coupling agents for surfactants and reservoir brines for the purpose of enhancing crude oil production. Surfactant and cosurfactant mixtures are dissolved in brines in low concentrations to form micellar fluids or solutions. These micellar solutions can be described as microemulsions containing surfactants which act to reduce the interfacial tension between water and oil. A second component, a cosurfactant, usually an alcohol, is used to improve the quality of the micellar solution. An efficient cosurfactant increases the micelles' capacity to solubilize more oil or water and still form stabilized solutions.

Compounds used as cosurfactants in the prior art have been alcohols such as isopropyl alcohol, amyl and hexyl alcohols and their ethoxylated derivatives. These cosurfactants have limited capabilities because of the variety of reservoir conditions encountered in enhanced oil recovery programs. For example, special systems must be designed for reservoirs which are essentially fresh water, that is, those which contain 6000 ppm or less monovalent ions, and those which are essentially hard water, those which contain 50,000 ppm monovalent ions plus 500 or more divalent ions. Cosurfactants should perform so as to achieve a stable fluid when the water-cosurfactant mixture is in contact or mixed with crude oil. Molecular weight of the cosurfactant should be sufficiently low to permit passage through semipermeable rock formations and achieve mobility control.

This invention accordingly relates to a new and unique family of low molecular weight polymers which are suitable for use as cosurfactants for enhanced crude oil recovery. These polymers in use lower the interfacial tension between water and oil, are low molecular weight, and are required in only low concentrations to formulate micellar fluids. This invention also relates to a method of preparing these low molecular weight polymers by photochemical reaction of aliphatic ketones with aliphatic and alicyclic olefins.

BACKGROUND OF THE INVENTION

This invention relates to low molecular weight olefin polymers and copolymers of 3-butene-1-ol, to a method for their preparation, and to their use as cosurfactants in crude oil recovery with micellar solutions.

Low molecular weight olefin polymers and copolymers of 3-butene-1-ol have not been previously known.

Photochemical reactions of olefins with ketones are known to result in cycloadditions. De Mayo, et al., *Can. J. Chem.*, 46, 2535–2547, teaches photochemical cycloaddition of cyclopentenone to a number of olefins. De Mayo indicated (p. 2538) that yield of desired cycloaddition product might depend on the concentration of cyclopentenone and that presumably at high enough concentration dimerization might become a competitive process. De Mayo however indicated cyclohexene dimer could not be detected in the cyclopentenone cycloaddition. Evidence suggested cyclopentenone reacts photochemically from two triplet states but only the higher leads to cycloaddition. Barltrop, et al., *J. Chem. Soc.*, D 1970 (23), 1637–8 (CA74:31374g) teaches photocycloaddition of alkyl ketones to conjugated dienes, i.e., ultraviolet irradiation of acetone and conjugated dienes such as butadiene gave vinyloxetanes by a mechanism involving the singlet excited state of the ketone. H. A. Carless, *Tetrahedron Letters*, 34, pp. 3173–3174, teaches that ultraviolet irradiation of acetone in the presence of olefins (2-methylpropene, 2-methylbut-2-ene or but-2-ene) leads to oxetanes as the major photoproducts.

In the absence of ultraviolet radiation, Boyce, et al., *J. Chem. Soc., Perkins Trans.* 1 1974 (7) 792–6 (CA81:63247d) teaches 1,1-diphenyl alkenes with carbonyl compounds underwent addition reactions exclusively at carbon-3, e.g., $(C_6H_5)_2C=CHCH_2CH_3$ with $(C_6H_5)_2CO$ gave $(C_6H_5)_2C=CHCH_2CH_2C(OH)(C_6H_5)_2$. U.S. Pat. No. 3,324,187 teaches a process for preparing fluorine-substituted olefinic alcohols by mixing under substantially anhydrous conditions a fluorine-substituted, perhalogenated acetone with an alpha-olefin having at least three carbon atoms in the olefinic chain. The resulting olefinic alcohols can be halogen substituted 3-butene-1-ol monomer compounds.

Accordingly, photochemical reactions of olefins with ketones to produce cycloaddition products are known, as well as non-photochemical reactions of ketones with olefins to produce 3-butene-1-ol monomers. However, photochemical reaction of aliphatic and alicyclic ketones with aliphatic ketones to produce low molecular weight 3-butene-1-ol olefin polymers and copolymers has not been known previously.

It is therefore an object of this invention to provide a process for preparation of low molecular weight 3-butene-1-ol olefin polymers and copolymers of molecular weight range from about 200 to about 4000 and a novel class of 3-butene polyhydroxy polymers and copolymers. Other objects and advantages will become apparent as the following description proceeds.

SUMMARY OF THE INVENTION

This invention relates to 3-butene-1-ol olefin polymers and copolymers of molecular weight from about 200 to about 4000 and a method for their preparation by reacting an olefinically unsaturated compound of from 3 carbon atoms to twelve carbon atoms and an aliphatic ketone of up to thirteen carbon atoms using actinic radiation as an energy source at a temperature of from 0° to 100° C., at a pressure of from 0.1 to 10 atmospheres. This invention also relates to a method for use of these polymers and copolymers as cosurfactants in micellar slugs for enhanced crude oil recovery.

DETAILED DESCRIPTION OF THE INVENTION

In general, this invention relates to novel 3-butene-1-ol olefin polymers and copolymers and to a method for their preparation represented as follows:

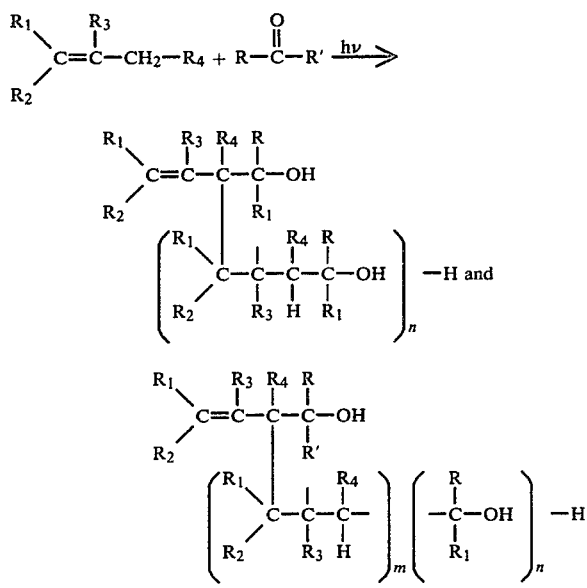

$R_1$, $R_2$, $R_3$, and $R_4$ are individually selected from the group consisting of hydrogen and alkyl groups of 1 to 9 carbon atoms, wherein the sum of carbon atoms of $R_1$, $R_2$, $R_3$ and $R_4$ does not exceed 9. R and R' are alkyl groups of from 1 to 11 carbon atoms wherein the sum of carbon atoms of R and R' does not exceed 12. Subscripts m and n are numbers from 1 to 10 and can be fractional, averaging a mixture of different integral m and n's that average to a fractional value. $R_1$ and $R_3$ can be joined as in an alicyclic olefin such as cyclohexene. R and R' can be joined as in an alicyclic ketone. The numbers m and n represent mixtures of similar products that differ by 1 or more repeating units and represent average ratios for the mixtures. The olefins can be straight-chain or branched-chain olefins containing 3 to 12 carbon atoms or cyclic olefins of up to 6 carbon atoms with the requirement that the olefin contain at least one $CH_2$-group in an alpha position to the olefinic double bond. Examples of olefins which can be used are propylene, 1-butene, 2-methyl-2-butene, 1-hexene, 4,4-dimethyl-1-butene, diisobutylene, cyclopentene and cyclohexene. Examples of ketones which can be used are acetone, 2-butanone, 2-pentanone, 3-pentanone, and 2- and 3-hexanones. Olefins of greater than 12 carbon atoms apparently are less suitable for use in this invention as low molecular weight polymers do not form readily when such are used in the instant process.

The molar ratios of the reactants, i.e., the ketones and olefins that can be used, can vary considerably. The ketone-olefin ratio can be between 1:10 to 10:1. In the practice of the invention, substantially equimolar amounts of ketone and olefin are preferred. Use of a solvent is not required although such use is convenient if solubility problems occur. Solvents such as heptane, hexane, benzene, at concentrations of 1 to 85 weight percent are convenient. In applications wherein solvents are used, phase transfer agents such as cetyl trimethyl ammonium chloride, benzyl triethyl ammonium chloride, benzyl triphenyl phosphorium chloride, etc., typically are incorporated at concentrations of 0.001 to 1% by weight of total solvent.

The reaction can be run in any type of open or sealed vessel, suitably agitated. A particularly useful apparatus for the reaction is a heavy-walled clear borosilicate glass or quartz bottle containing a low-pressure, medium-pressure, or high-pressure mercury arc lamp capable of emitting light of wave lengths 1800–3000 Å. A preferred source is a low-pressure mercury arc lamp in a quartz coil emitting light energy almost entirely at 1850 Å and 2537 Å. The reaction can be run at temperatures of from 0° C. to 100° C., preferably 20° to 40° C., at pressures of 0.1 to about 10 atmospheres for periods of 1 to 200 hours. Typically, the reaction is run at room temperature, atmospheric pressure, and for periods of from 12 to 100 hours.

Reaction is continued until the required amount of polymer has been obtained, as shown by analysis of samples. Workup generally consists of distilling the reaction mixture at 100°–200° C. at reduced pressure, 100–200 mm mercury, to recover unreacted materials.

In summary, the present invention comprises a process for preparing olefin polymers and copolymers of 3-butene-1-ol by reacting an olefinically unsaturated compound of three to 12 carbon atoms and an aliphatic ketone of from 3 to 13 carbon atoms using actinic radiation as an energy source within the range of from 1800 Å to 3000 Å, wherein molar ratio of said olefin and said ketone is within the range of 10:1 to 1:10, at a temperature within the range of 0° C. to 100° C. and a pressure of from 0.1 to 10 atmospheres.

The present invention also comprises a composition which it is believed can be structurally represented as containing repeating units as follows:

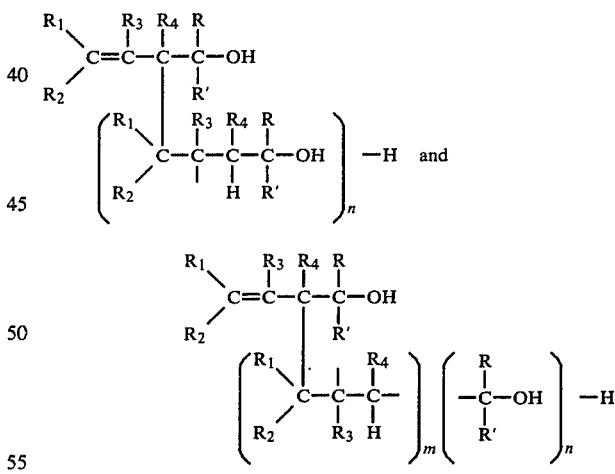

While it is believed that the above structural representations of the compositions are accurate, these representations are presented for purposes of illustration only and are not intended to limit the scope of the invention.

The present invention also comprises a method of injecting a micellar slug into a subterranean formation comprising the steps of (1) contacting said subterranean formation with an aqueous fluid composition comprising water, a surfactant, a hydrocarbon, an electrolyte and a low molecular weight polymer selected from the group consisting of an olefin polymer and copolymer of 3-butene-1-ol, (2) applying sufficient pressure to said composition to cause said micellar slug to move through said formation, (3) maintaining sufficient pressure while injecting said composition into said formation. The said low molecular weight polyme can be selected from the group consisting of polymers prepared from 1-hexene and 2-butanone, 1-hexene and 3-pentanone and 3-pentanone and 1-heptene.

In order to facilitate a clear understanding of the invention, the process of preparing low molecular weight olefin polymers and copolymers of 3-butene-1-ol, the instant polymers of molecular weights of 200 to 4000, and the use thereof, the following specific embodiments are described in detail. It should be understood, however, that the detailed expositions of the instant invention, while indicating preferred embodiments, are given by way of illustration only since various changes and modifications within the spirit and scope of the invention will become apparent to those skilled in the art from this detailed description.

PRELIMINARY EXAMPLE

Screening tests for suitable cosurfactants to be used as additives for enhanced oil recovery have been developed which indicate a relationship exists between interfacial tension of the cosurfactant and petroleum removal from core samples using a micellar solution. Surfactant-stabilized dispersions of water in hydrocarbon are micellar solutions. In addition to the required surfactant, water and hydrocarbon, micellar solutions can contain cosurfactants and electrolytes to improve stability. Alcohols such as isopropanol and amyl alcohols typically have served as cosurfactants. Sodium chloride and sodium sulfate are examples of electrolytes which are used.

Important aspects of a micellar solution include an ability to solubilize water, compatability with hydrocarbon and crude oil, an increasing viscosity with increased water concentration and inversion to an oil-in-water solution. In a micelle, surfactant and cosurfactant surround dispersed water which exists in the hydrocarbon phase as spherical droplets. With additional water, the water droplets increase in size. When water is the dispersed phase, the micellar solutions exhibit hydrocarbon-like properties of the external phase. As more and more water is solubilized in a micellar system, spheres enlarge until inversion takes place to form an oil-in-water emulsion. Cosurfactants in a micellar solution stabilize the solution to reduce incidence of inversion and phase separation.

The following bench test has been devised as a preliminary vial-screen test to eliminate need for expensive core tests of cosurfactants. The test has been found to have reliability in predicting suitable properties of cosurfactants when used in micellar solutions. The principal important aspect has been found to be the interfacial tension of the cosurfactant in an oil-water mixture. The formulation is required to yield stable fluids in brine and to show low interfacial tension (IFT) as well as very good miscibility with crude petroleum.

Micellar fluids formulated from concentrates containing 40:1 to 5:1 surfactant-cosurfactant ratios have been tested over a wide range of salinities (sodium chloride in water) and hard waters, being examined for phase stability, fluid clarity, interphase behavior and miscibility of aqueous fluids with crude petroleum.

The vial-screening bench test is an empirical test which comprises mixing the micellar fluid and crude petroleum by swirling the fluids together in a test tube while observing the interface. A light source is used to observe the fluid-oil behavior. The interfacial mixing (and hence interfacial tension) is judged upon a scale of very low, moderately low, low, medium and high by a comparison with standards previously developed.

For example, brine solutions of a hardness range from under 6,000 ppm of monovalent ions (sodium chloride) to about 50,000 ppm of monovalent ions (sodium chloride) plus 500 ppm of divalent ions (calcium chloride) are mixed with a 40:1 ratio of surfactant-cosurfactant mixture with Second Wall Creek crude. Surfactant is a petroleum sulfonate. Surfactant-cosurfactant-brine mixtures are prepared at ambient temperature and pressure.

Stability of the brine solution with surfactant-cosurfactant mixture is tested by pouring the mixture into a 50 ml graduated cylinder and allowing the solution to stand for one hour undisturbed. Fluids which remained single phase and free of sediment are further tested. 20 ml of solution are poured into a vial. 4 ml of crude petroleum are added to the vial. The vial is turned gently, observing mixing behavior of crude and micellar fluid. The vial is then shaken vigorously for one minute, after which the vial is allowed to stand undisturbed for one hour. After this period, the fluid is evaluated for oil drop-out, number of liquid phases, thickness of emulsion and miscibility. Results are correlated with interfacial tension of solution and crude by visual observation and spinning drop method of J. L. Caylas, et al., "Low Interfacial Tension," American Chemical Society Series No. 8, *Adsorption At Interfaces*, 1975. Formation of round oil droplets which separate quickly and failure to form an emulsion indicates a high, ineffective interfacial tension characteristic which can render the cosurfactant unsuitable as an additive for enhanced oil recovery applications.

EXAMPLE I

A mixture of 145.2 ml (1.1 moles) of 1-hexene and 98.5 ml (1.1 moles) of 2-butanone was stirred and irradiated with a low-pressure mercury coil emitting radiation almost entirely at 1850 Å and 2537 Å for 45 hours at 30° C. The mixture was distilled to a pot temperature of 140° C. at 200 mm to recover 152 ml of unreacted 1-hexene plus 2-butanone, and leave a residue of 69 g of water-white, viscous liquid with a pleasant, sweet aroma. It analyzed 78.2% C, 12.0% H, and 9.9% O (by difference), and had a bromine number of 182 mg $Br_2$/gram sample.

Analysis by nuclear magnetic resonance demonstrated the presence of tertiary alcohol groups and olefin resonances, mainly terminal, with some internal due to isomerization by UV light. Molecular weight on the basis of the bromine number was 879. The unit comprising one molecule of olefin plus one molecule of ketone had a calculated molecular weight of 156; found by oxygen analysis, 163. The structure of the product was represented as

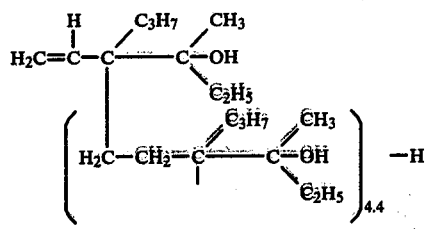

EXAMPLE II

A mixture of 116.2 ml (1.1 moles) of 3-pentanone, diethyl ketone, and 137.5 ml (1.1 moles) of 1-hexene was stirred at 25° C. and irradiated with a low-pressure mercury coil emitting radiation almost entirely at 1850 Å and 2537 Å for 46 hours. The mixture was distilled to a pot temperature of 165° C./200 mm to recover unreacted material, 114 ml, and obtain 91.2 g of viscous, water-white, sweet-smelling liquid product that analyzed 77.8% C, 12.8% H, 9.4% O, and had a bromine number of 167 mg. bromine/g of product. Molecular weight, basis bromine number, was 958. From infrared and nmr spectroscopy, elemental analysis and bromine number the product had the structure

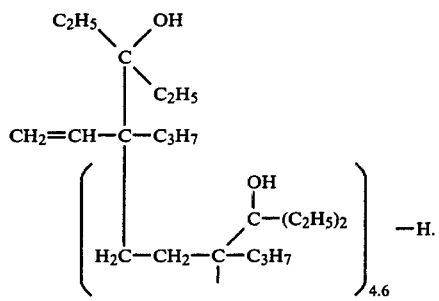

EXAMPLES III–XXI

In the procedure of Examples I and II, Examples III to XXI were performed. Molecular weights calculated on the basis of bromine numbers, were within the range of from about 200 to 4000. Details are in Table I.

TABLE I
LOW MOLECULAR WEIGHT POLYMERS OF 3-BUTENE-1-OL

| Example | Olefin (moles)[a] | Ketone[b] | Hrs | Wt. of Product g | Br # | Mol Wt |
|---|---|---|---|---|---|---|
| III | 1-Hexene (1.4) | A | 18 | 56.9 | 344 | 465 |
| IV | 1-Heptene (1.1) | 3-P | 46 | 94.5 | 143 | 1120 |
| V | 1-Octene (1.1) | A | 72 | 107.8 | 157 | 1020 |
| VI | Propylene[c] | 3-P | 14 | 16.2 | 100 | 1000 |
| VII | 2-Methyl-2-Butene (1.4) | A | 13 | 17.6 | 398 | 403 |
| VIII | Cyclohexene (1.4) | A | 17 | 61.0 | 638 | 250 |
| IX | 4-Methyl Cyclohexene (1.3) | A | 18 | 30.4 | 580 | 279 |
| X | 4-Methyl Cyclohexene (1.2) | 2-B | 45 | 58.6 | 390 | 410 |
| XI | Cycloheptene (1.1) | 3-P | 72 | 77.7 | 181 | 886 |
| XII | Propylene[c] | 2-P | 25 | 9 | 124 | 1310 |
| XIII | 1-Pentene (1.4) | A | 48 | 30.9 | 330 | 486 |
| XIV | Cyclopentene (1.5) | A | 48 | 38.8 | 663 | 241 |
| XV | Diisobutylene (1.2) | A | 47 | 14.5 | 319 | 501 |
| XVI | Diisobutylene (1.1) | 2-B | 72 | 21.5 | 281 | 569 |
| XVII | Diisobutylene (1.0) | 3-P | 72 | 25.6 | 232 | 689 |
| XVIII | 2-Methyl-1-Butene (1.4) | 2-B | 20 | 15.6 | 549 | 291 |
| XIX | 1-Decene (1.0) | A | 69 | 42.7 | 51 | 3118 |
| XX | Polyisobutylene (351 mol. wt.) (0.5) | 2-B | 168 | 185.9 | 165 | 969 |
| XXI | 1-Dodecene (0.75) | A | 72 | 40.6 | 193 | 984 |

Conditions
[a]Equimolar quantities of olefin and ketone except Example XXI of 0.75:0.88.
[b]A = acetone; 2-B = 2-butanone; 2-P = 2-pentanone; 3-P = 3-pentanone.
[c]Ketone saturated with propylene at 25° C., then propylene bubbled through mixture at 100 cc/min. during irradiation.

EXAMPLE XXII

Interfacial tension of representative low molecular weight polymers of Examples I to XXI were determined at 1 (wt)% concentration between solvent-extracted 5W oil and water, using a Cenco-Du Nouy Interfacial Tensiometer #70545 with a 6 cm platinum-iridium ring at 25° C. with double distilled water, with these results:

| Product of Example # | Interfacial Tension, dynes/cm |
|---|---|
| Control | 40.5 |
| I | 22.5 |
| II | 19.8 |
| III | 22.0 |
| IV | 20.4 |
| V | 23.4 |
| VI | 28.5 |
| VIII | 15.7 |
| IX | 19.6 |
| X | 18.3 |
| XII | 26.7 |
| XIII | 22.0 |
| XIX | 28.8 |
| XXI | 23.4 |

EXAMPLE XXIII

Representative low molecular weight polymers were tested in the vial test as cosurfactants for enhanced oil recovery, using 5% petroleum sulfonate as surfactant in 0.8 N brine (NaCl), adding the cosurfactant to surfactant at a ratio of 1:20, and noting the stability of the mixture, as brine tends to cause the surfactant to separate (salt) out. The brine-surfactant-cosurfactant mixture, 20 ml, was then mixed by shaking with 2.5 ml of crude petroleum and the interfacial tension (IFT) observed. Low IFT was indicated by easy mixing of the two phases with no separation. Formation of round oil droplets that separate quickly indicates a high, ineffective IFT.

Products of Examples I, II and IV proved effective in lowering the IFT in the vial test, giving mixtures of brine-surfactant-cosurfactant fluids which were stable, did not separate, and easily formed mixtures of the fluid with crude petroleum.

EXAMPLE XXIV

Control of microorganisms in inhibiting or preventing growth of fungi in enhanced oil recovery operations is a desirable characteristic of useful additives.

The products of this invention were tested as biocides and inhibitors for the growth of microorganisms by this test: 25 g of agar preparation were placed in standard Petri dishes. The agar preparation consisted of 23.5 g of Bacto Plate Count Agar, Difco Laboratories, Detroit, Mich., dissolved in 1 liter of water. Plate count Agar contains a standard USP formula for nutrient agar, consisting of

| | |
|---|---|
| 5 g | Pancreatic digest of casein |
| 2.5 g | Yeast extract |
| 1 g | Glucose |
| 15 g | Agar |

Four Petri dishes were untreated and used as blanks. To the others, in duplicate, were added 2.5 ml of 1% acetone solutions of the products of Examples I–XX.

All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results were as follows:

| Product of Example No. | Growth |
| --- | --- |
| Control | 5,5,5,5 |
| I | 4,5 |
| II | 3,3 |
| III | 0,0 |
| IV | 0,0 |
| V | 0,1 |
| VI | 0,0 |
| VII | 0,0 |
| VIII | 0,0 |
| IX | 0,0 |
| X | 0,0 |
| XI | 0,0 |
| XII | 0,0 |
| XIII | 0,0 |
| XIV | 0,0 |
| XV | 0,0 |
| XVI | 0,0 |
| XVII | 0,0 |
| XVIII | 0,0 |
| XIX | 0,0 |
| XX | 4,5 |

EXAMPLE XXV

A micellar slug for micellar flooding consisting of 3 (vol)% petroleum sulfonate as surfactant, 2 (vol)% petroleum hydrocarbon, 1 (vol)% cosurfactant comprising a polymer of 3-butene-1-ol, prepared from 1-hexene and 2-butanone, molecular weight 879, in a 1.0 N NaCl brine solution is prepared. The micellar slug fluid is fed into the high pressure injection pump and is injected into a 25 foot section sandstone formation in Crawford County, Ill., through an injection well at 900 psig. The amount of slug injected is about 7% of reservoir pore volume and the petroleum hydrocarbon is lease crude oil. Pattern of injection is two rows of injection wells and three rows of producer wells. There are nine wells in each row and total area enclosed is 40 acres. Injection and production wells are 460 feet apart and adjacent wells are 115 feet apart. Crude oil production increases to recover about 30% of the oil in place at start of the injection.

What is claimed is:

1. A composition structurally represented as containing repeating units as follows:

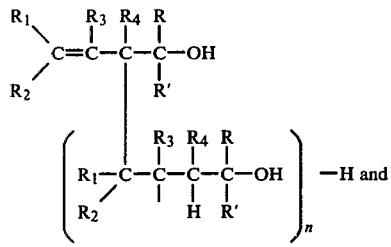 —H and

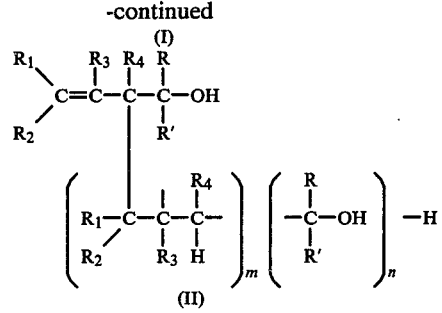

wherein m and n are fractional and whole numbers from 1 to 10, $R_1$, $R_2$, $R_3$ and $R_4$ are individually selected from the group consisting of hydrogen and alkyl groups of 1 to 9 carbon atoms, wherein the sum of carbon atoms of $R_1$, $R_2$, $R_3$ and $R_4$ does not exceed 9, R and R' are alkyl groups of from 1 to 11 carbon atoms wherein the sum of carbon atoms of R' and R does not exceed 12 wherein $R_1$ and $R_3$ can be joined to form an alicyclic olefin.

2. The composition of claim 1 wherein $R_1$, $R_2$, $R_3$, $R_4$ are hydrogen and R and R' are methyl groups.

3. The composition of claim 1 wherein $R_1$, $R_2$ and $R_3$ are hydrogen, $R_4$ is an alkyl group of from 1 to 9 carbon atoms, R and R' are alkyl groups of 1 to 6 carbon atoms.

4. The composition of claim 1 wherein said repeating units are reaction products of an olefinically unsaturated compound of 3 to 12 carbon atoms selected from the group consisting of aliphatic and alicyclic olefins of the structure

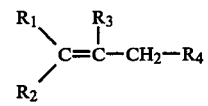

wherein $R_1$, $R_2$, $R_3$ and $R_4$ are individually selected from the group consisting of hydrogen and alkyl groups of 1 to 9 carbon atoms wherein the sum of carbon atoms of $R_1$, $R_2$, $R_3$ and $R_4$ does not exceed 9 and an aliphatic ketone of 3 to 8 carbon atoms of the structure

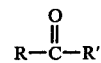

wherein R and R' are alkyl groups.

5. The composition of claim 4 wherein said olefinically unsaturated compound is selected from the group consisting of propylene, 1-butene, cis- and trans-2-butene, isobutylene, 1- and 2-pentene, 2-methyl-1-butene, 2-methyl-2-butene, 1-hexene, 4,4-dimethyl-1-butene, diisobutylene, cyclopentene, cyclohexene, cycloheptene, cyclooctene, 4-methylcyclohexene, 4-tert-dodecylcyclohexene and 4-tert-butylcycloheptene.

6. The composition of claim 4 wherein said aliphatic ketone is selected from the group consisting of acetone, 2-butanone, 2-pentanone, 3-pentanone.

7. A process for preparing olefin polymers and copolymers of 3-butene-1-ol by reacting an olefinically unsaturated compound of 3 to 12 carbon atoms of the structure

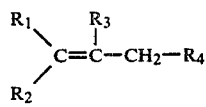

wherein $R_1$, $R_2$, $R_3$ and $R_4$ are individually selected from the group consisting of hydrogen and alkyl groups of 1 to 9 carbon atoms wherein the sum of carbon atoms of $R_1$, $R_2$, $R_3$ and $R_4$ does not exceed 9 and an aliphatic ketone of from 3 to 13 carbon atoms of the structure

wherein R and R' are alkyl groups of from 1 to 11 carbon atoms wherein the sum of carbon atoms of R and R' does not exceed 12, using actinic radiation as an energy source within the range of from 1800 Angstroms to 3000 Angstroms, wherein molar ratio of said olefin and said ketone is within the range of 10:1 to 1:10, at a temperature within the range of 0° C. to 100° C. and a pressure of from 0.1 to 10 atmospheres.

8. The process of claim 7 wherein said ketone is selected from the group consisting of acetone, 2-butanone, 2-pentanone, 3-pentanone.

9. The process of claim 7 wherein said olefin is selected from the group consisting of propylene, 1-butene, cis- and trans-butene, isobutylene, 1- and 2-pentene, 2-methyl-1-butene, 2-methyl-2-butene, 1-hexene, 4,4-dimethyl-1-butene, diisobutylene, cyclopentene, cyclohexene, cycloheptene, cyclooctene, 4-methylcyclohexene, 4-tert-dodecylcyclohexene, and 4-tert-butylcycloheptene.

10. The process of claim 7 wherein molar ratio of said olefin and said ketone is 1:1, temperature is within range of 20° to 40° C. and pressure is 1 atmosphere.

11. A composition comprising olefin polymers and copolymers of 3-butene-1-ol prepared by reacting an olefinically unsaturated compound of 3 to 12 carbon atoms selected from the group consisting of aliphatic and alicyclic olefins of the structure

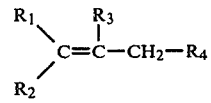

wherein $R_1$, $R_2$, $R_3$ and $R_4$ are individually selected from the group consisting of hydrogen, and alkyl groups of 1 to 9 carbon atoms, wherein the sum of carbon atoms of $R_1$, $R_2$, $R_3$ and $R_4$ does not exceed 9 and an aliphatic ketone of 3 to 13 carbon atoms of the structure

wherein R and R' are alkyl groups of from 1 to 11 carbon atoms wherein the sum of carbon atoms of R and R' does not exceed 12, using actinic radiation as an energy source within the range of from 1800 Angstroms to 3000 Angstroms, wherein molar ratio of said olefin and said ketone is within the range of 10:1 to 1:10, at a temperature within the range of 0° C. to 100° C. and a pressure of from 0.1 to 10 atmospheres.

12. The composition of claim 11 wherein said ketone is selected from the group consisting of acetone, 2-butanone, 2-pentanone, 3-pentanone.

13. The composition of claim 11 wherein said olefin is selected from the group consisting of propylene, 1-butene, cis- and trans-butene, isobutylene, 1- and 2-pentene, 2-methyl-1-butene, 2-methyl-2-butene, 1-hexene, 4,4-dimethyl-1-butene, diisobutylene, cyclopentene, cyclohexene, cycloheptene, cyclooctene, 4-methylcyclohexene, 4-tert-dodecylcyclohexene, and 4-tert-butylcycloheptene.

14. The composition of claim 11 wherein molar ratio of said olefin and said ketone is 1:1, temperature is within range of 20° to 40° C. and pressure is 1 atmosphere.

15. A process for preparing olefin polymers and copolymers of 3-butene-1-ol by reacting under suitable photochemical conditions an olefinically unsaturated compound of 3 to 12 carbon atoms of the structure

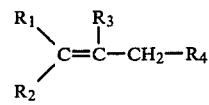

wherein $R_1$, $R_2$, $R_3$ and $R_4$ are individually selected from the group consisting of hydrogen and alkyl groups of 1 to 9 carbon atoms, wherein the sum of carbon atoms of $R_1$, $R_2$, $R_3$ and $R_4$ does not exceed 9 and an aliphatic ketone of from 3 to 13 carbon atoms of the structure

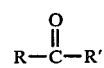

wherein R and R' are alkyl groups of from 1 to 11 carbon atoms wherein the sum of carbon atoms of R and R' does not exceed 12, wherein molar ratio of said olefin and said ketone is within the range of 10:1 to 1:10.

16. The process of claim 15 wherein said ketone is selected from the group consisting of acetone, 2-butanone, 2-pentanone, 3-pentanone.

17. The process of claim 15 wherein said olefin is selected from the group consisting of propylene, 1-butene, cis- and trans-butene, isobutylene, 1- and 2-pentene, 2-methyl-1-butene, 2-methyl-2-butene, 1-hexene, 4,4-dimethyl-1-butene, diisobutylene, cyclopentene, cyclohexene, cycloheptene, cyclooctene, 4-methylcyclohexene, 4-tert-dodecylcyclohexene, and 4-tert-butylcycloheptene.

18. The process of claim 15 wherein molar ratio of said olefin and said ketone is 1:1.